US008645059B2

(12) United States Patent
Tuulari

(10) Patent No.: US 8,645,059 B2
(45) Date of Patent: Feb. 4, 2014

(54) METHOD OF GENERATING GRAPHICAL DATA AND ELECTRONIC DEVICE

(75) Inventor: Esa Tuulari, Kempele (FI)

(73) Assignee: Polar Electro Oy, Kempele (FI)

( * ) Notice: Subject to any disclaimer, the term of this patent is extended or adjusted under 35 U.S.C. 154(b) by 1354 days.

(21) Appl. No.: 12/254,955

(22) Filed: Oct. 21, 2008

(65) Prior Publication Data

US 2009/0115618 A1   May 7, 2009

(30) Foreign Application Priority Data

Nov. 1, 2007 (FI) .................................. 20075778

(51) Int. Cl.
G01S 19/19 (2010.01)
(52) U.S. Cl.
USPC ........ 701/467; 701/521; 701/491; 340/573.1; 342/357.57; 702/182
(58) Field of Classification Search
None
See application file for complete search history.

(56) References Cited

U.S. PATENT DOCUMENTS 6,321,158 B1 * 11/2001 DeLorme et al. ............. 701/426
6,798,378 B1 *  9/2004 Walters ..................... 342/357.57
7,254,483 B2 *  8/2007 Squires et al. ..................... 702/2
7,254,516 B2     8/2007 Case, Jr. et al.
7,292,867 B2 * 11/2007 Werner et al. .............. 455/456.3
7,805,149 B2 *  9/2010 Werner et al. .............. 455/456.3
2004/0209600 A1   10/2004 Werner et al.
2005/0102931 A1    5/2005 Ringness
2007/0063850 A1 *  3/2007 Devaul et al. ............. 340/573.1
2008/0319661 A1 * 12/2008 Werner et al. ................. 701/211
2009/0030551 A1 *  1/2009 Hein et al. .................... 700/253
2012/0202530 A1 *  8/2012 Sheha et al. .................. 455/457
2013/0218456 A1 *  8/2013 Zelek et al. ................... 701/412

FOREIGN PATENT DOCUMENTS

WO   WO2005031272 A1   4/2005

* cited by examiner

Primary Examiner — Thomas Black
Assistant Examiner — Paul Castro
(74) Attorney, Agent, or Firm — Hoffmann & Baron, LLP

(57) ABSTRACT

There is provided an electronic device, comprising: a receiving unit configured to receive location data generated by a navigation unit of a positioning system, and to receive performance data from a measuring unit, wherein performance parameters of the performance data are associated to corresponding route points included in the received location data; and a graphic generator configured to generate graphical data associated to the received location data. The graphic generator is further configured to generate graphical data associated to the performance parameters; and to adjust the spatial dimension of the generated graphical data associated to the performance parameters in proportion to the corresponding route points of the received location data on the basis of the values of the performance parameters.

21 Claims, 5 Drawing Sheets

METHOD OF GENERATING GRAPHICAL DATA AND ELECTRONIC DEVICE

CROSS-REFERENCE TO RELATED APPLICATION

This application claims priority based on Finnish Patent Application No. 20075778, filed Nov. 1, 2007, which is incorporated herein by reference.

BACKGROUND OF THE INVENTION

The invention relates to a method of generating graphical data, to an electronic device, and to a computer-readable distribution medium.

DESCRIPTION OF THE RELATED ART

Location data received from satellite navigation systems have been used for generating different graphical data associated to the received location data. Further, monitoring a course of a physical exercise (e.g. running, skiing, cycling exercise) on a certain route has been enabled by using information received from a satellite navigation system and performance information from a measuring device. Thus, for example monitoring changes of a heart rate or speed of a person jogging a certain route is possible. One prior art solution generates graphical data of a travelled route and indicates this route with different colors depending on the heart rate values in certain parts of the route.

One of the problems with this known solution is that only a limited amount of information can be indicated at a time. For example, if a person would like to monitor both heart rate values and speed during the travelled route, he/she would be forced to create different graphical data presentations for each of them. Further, it can be difficult to understand how e.g. the heart rate value changes based on different colors. The user would at least be forced to memorize which values are illustrated by which colors. Accordingly, it is useful to find more user-friendly and effective techniques for generating graphical data associated to location data and user performance data.

SUMMARY OF THE INVENTION.

An object of the present invention is to provide an improved method, an electronic device, and a computer-readable distribution medium. The objects of the invention are achieved by a method and an electronic device, which are characterized by what is stated in the independent claims.

According to an aspect of the invention, there is provided an electronic device, comprising: a receiving unit configured to receive location data generated by a navigation unit of a positioning system, and to receive performance data from a measuring unit, wherein performance parameters of the performance data are associated to corresponding route points included in the received location data; and a graphic generator configured to generate graphical data associated to the received location data. The graphic generator is further configured to generate graphical data associated to the performance parameters; and to adjust the spatial dimension of the generated graphical data associated to the performance parameters in proportion to the corresponding route points of the received location data on the basis of the values of the performance parameters.

According to another aspect of the invention, there is provided a method of generating graphical data, the method comprising: receiving location data generated by a navigation unit of a positioning system; receiving performance data from a measuring unit, wherein performance parameters of the performance data are associated to corresponding route points included in the received location data; and generating graphical data associated to the received location data. The method further comprises generating graphical data associated to the performance parameters; and adjusting the spatial dimension of the generated graphical data associated to the performance parameters in proportion to the corresponding route points of the received location data on the basis of the values of the performance parameters.

According to another aspect of the invention, there is provided computer-readable distribution medium encoding a computer program of instructions for executing a computer process, the process comprising: receiving location data generated by a navigation unit of a positioning system; receiving performance data from a measuring unit, wherein performance parameters of the performance data are associated to corresponding route points included in the received location data; and generating graphical data associated to the received location data. The process further comprises: generating graphical data associated to the performance parameters; and adjusting the spatial dimension of the generated graphical data associated to the performance parameters in proportion to the corresponding route points of the received location data on the basis of the values of the performance parameters.

The invention is based on adjusting the spatial dimension of generated graphical data associated to the performance parameters in proportion to the corresponding route points of received location data on the basis of the values of the performance parameters.

The electronic device and method of the invention provide several advantages. The amount of graphical information in the generated graphical data can be increased effectively. More than one kind of performance data can be easily associated with one route graph. Thus, user-friendliness is improved. Quantitative information can be easily monitored from the generated graphical data.

BRIEF DESCRIPTION OF THE DRAWINGS

In the following the invention will be described in greater detail with reference to the embodiments and the accompanying drawings, in which.

DETAILED DESCRIPTION OF THE EMBODIMENTS

Figure 1:
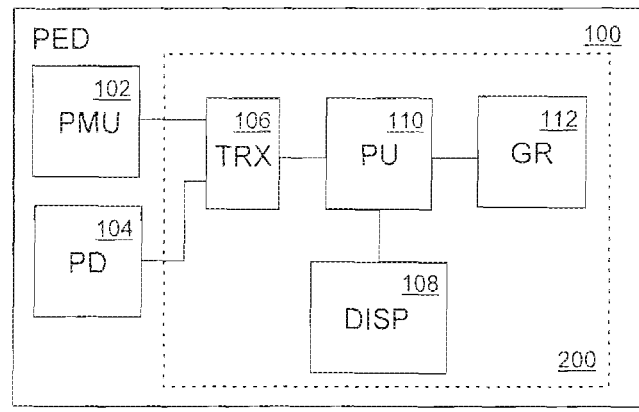
FIG. 1 shows an example of the structure of an arrangement according to an embodiment.

With reference to FIG. 1, we now examine an example of an arrangement to which embodiments of the invention can be applied. The embodiments are, however, not restricted to this arrangement described only by way of example, but a person skilled in the art can apply the instructions to other arrangements containing corresponding characteristics.

The arrangement 100 of FIG. 1 comprises a satellite navigation unit 104, a performance-measuring unit 102, a receiving unit 106, a processing unit 110, a graphic generator 112 and a display unit 108. The different elements of this arrangement 100 may be separate devices that can communicate with one or more other elements of the arrangement. In the example of FIG. 1, the receiving unit 106, the processing unit 110, the graphic generator 112 and the display unit 108 are physically included in a single electronic device 200, and the satellite navigation unit 104 and the performance-measuring unit 106 form their own entities that communicate with the electronic device 200 with wired or wireless connections. However, the satellite navigation unit 104 and/or the performance-measuring unit 106 may also be parts of the electronic device 200.

The satellite navigation unit 104 of FIG. 1 is for providing position/location data. Different satellite navigation systems provide geo-spatial positioning with global coverage. Such systems enable this kind of small electronic receivers 104 to determine their location (longitude, latitude and altitude) to within a few metres using time signals transmitted along a line of sight by radio from satellites. Examples of current global navigation systems include, for example, a GPS (Global Positioning System) and GLONASS (Global Navigation Satellite System). Other near future systems include Compass navigation system, DORIS (Doppler Orbitography and Radio-positioning Integrated by Satellite), Galileo Positioning System, IRNSS (Indian Regional Navigational Satellite System), and QZSS (Quasi-Zenith Satellite System).

The performance-measuring unit 102 is configured to measure performance data of a user of the device. The measured performance data may comprise performance parameters including at least one of the following values: heart rate, heart rate variation, any threshold value, velocity, reciprocal of velocity, pedalling power, cadence, pace frequency, an activity parameter, pulse, power level, step length, fitness value, body temperature, colliquation state, performance capacity index, lactic acid state, any physiological parameter, or any ratio thereof, or any combination thereof. Any suitable methods and elements, such as pulse detectors and acceleration sensors, can be used to measure these performance parameters.

In an embodiment, the performance parameter characterizes the type of performance. The type of performance may include the style of propagation, such as skiing style, walking, running and biking.

In an embodiment, the type of performance characterizes a swimming style and the length and timing of hand strokes.

Figure 3:
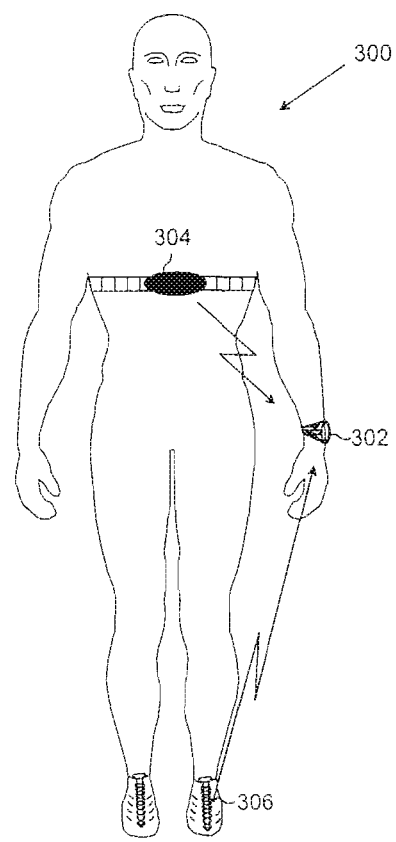
FIG. 3 shows an example of an electronic device according to an embodiment.

In an embodiment, the performance-measuring unit 102 may comprise or be a part of a wrist device that may be the wrist device 302 of a performance monitor shown in FIG. 3. A performance monitor may comprise not only the wrist device 302, but also one or more auxiliary devices 304, 306, such as a motion sensor 306 fastened to a limb of the user 300 of the device and/or a pulse transmitter 304 indicating electric pulses induced by the heart. The auxiliary device 304, 306 may communicate over wired or wireless connections with the wrist device 302. In an embodiment, the motion sensor 306 comprises an acceleration sensor that measures the acceleration related to the movement of the user 300. The acceleration sensor transforms the acceleration caused by a movement or gravity into an electric signal.

The performance-measuring unit 102 may also comprise a pre-processing unit for processing primary performance data, such as acceleration data and/or vibration data. The processing may comprise transforming primary motion data into secondary motion data, for instance transforming acceleration data related to a user-generated movement into motion pulse data. The processing may also comprise filtering primary and/or secondary performance data.

The receiving unit 106 is configured to receive the measured location data and the performance data. The satellite navigation unit 104 and the performance-measuring unit 102 may communicate with the receiving unit 106 over wireless or wired connections. It is possible that the electronic device 200 is a personal computer, a PDA (Personal Digital Assistant) device, a handheld computer, or any portable device and the data from the satellite navigation unit 104 and the performance data are loaded to the device for further processing. It is also possible that the data from the satellite navigation unit 104 and the performance-measuring unit 102 is directly and continuously delivered to the receiving unit 106 while the data is being determined in the satellite navigation unit 104 and the performance-measuring unit 102.

In an embodiment, the satellite navigation unit 104 is configured to determine and store location data and the performance-measuring unit 102 is configured to measure and store performance data continuously for a certain period of time, after which the stored location data and the performance data are transferred to the receiving unit 106. It is also possible that the determined location data and/or the performance data is not stored in the satellite navigation unit 104 or in the performance-measuring unit 102 but is continuously communicated via a communication connection to the receiving unit 106.

The processing unit 110 comprises a digital signal processor and executes a computer process according to encoded instructions stored in a memory. The processing unit 110 may be implemented by using analog circuits, ASIC circuits (Application Specific Integrated Circuit), a digital processor, a memory and computer software. The processing unit 110 may constitute part of the computer of a wrist device 302, for example.

The performance parameters of the received performance data are associated to corresponding route points included in the received location data. This means that during a physical exercise in which a user is travelling a certain route, each performance parameter measured is associated to the corresponding route point where the measuring took place. The performance parameters can be measured at predetermined intervals during the exercise or continuously. The user of the device can determine how the performance parameters are measured. There may also be different measurement settings pre-programmed in the device. The route points may also include such route points that are interpolated or extrapolated based on received location data. Accordingly, the performance data can be interpolated/extrapolated between different route points.

The graphic generator 112 is configured to generate graphical data associated to the received location data, and to generate graphical data associated to the performance parameters. In an embodiment, the graphic generator 112 is further configured to adjust the spatial dimension of the generated graphical data associated to the performance parameters in proportion to the corresponding route points of the received location data on the basis of the values of the performance parameters.

In an embodiment, the graphic generator 112 is configured to include instructions on the details of the graphics in the generated graphical data associated to the received location data and the generated graphical data associated to the performance parameters.

The display unit 108, that may contain LCD (Liquid Crystal Display) components, for instance, may indicate the generated graphical data graphically and/or numerically to the user 300, e.g. according to the instructions included in the graphical data.

Figure 2:
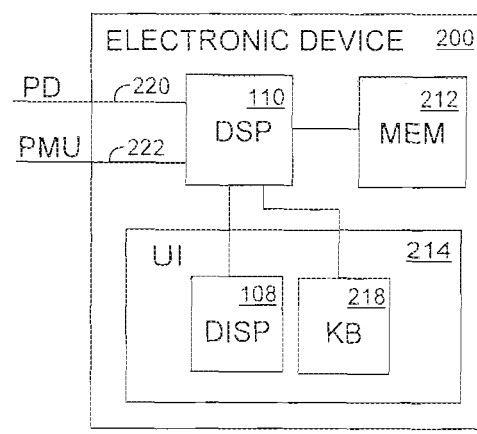
FIG. 2 shows another example of the structure of an electronic device according to another embodiment.

FIG. 2 shows another example of the structure of an electronic device 200 according to an embodiment. The electronic device 200 typically comprises a processing unit 110, a memory unit 212, and user interface parts 214. The electronic device 200 may be, for example, a personal computer, a wrist device 302 or a device carried on a bicycle.

The processing unit 110 receives location data 220 from a satellite navigation unit, and performance data 222 from a measuring unit, wherein performance parameters of the performance data are associated to corresponding route points included in the received location data. The association of the performance parameters to the corresponding route points can be executed in the processing unit 110 or in any another processing device, for example in the satellite navigation unit 104, the performance-measuring unit 104 or in the wrist device 302.

The processing unit 110 controls the functions of the electronic device 200 and it may execute computer processes according to encoded instructions stored in the memory unit 212. The graphic generator of FIG. 1 may be a part of the processing unit 110.

The user interface 214 typically comprises a display unit 108 and a display controller. The user interface 214 may further comprise a keypad 218 allowing the user to input commands in the electronic device 200. The display unit 108 is configured to indicate the generated graphical data associated to the received location data and the generated graphical data associated to the performance parameters. The display unit 108 may follow the instructions included in the generated graphical data for indicating the graphics on a display. In an embodiment, the graphical data associated to the performance parameters includes instructions on indicating the graphical data associated to the performance parameters in the form of at least one of the following graphical data items: a column, a pillar, a line, a point, a pattern, or any combinations thereof.

In an embodiment, the electronic device 200 may comprise a pulse counter, in which case the electronic device 200 receives a signal 222 transmitted from the performance-measuring unit 102. The performance-measuring unit 102 may, for example, be a belt-like structure installed on the user's chest and comprising means for performing an electrocardiogram measurement (ECG) and for transmitting ECG information to the electronic device 200.

In an embodiment, the processing unit 110 is configured to generate graphical data including graphical data items associated to the performance parameters, wherein the spatial dimension of each graphical data item associated to the corresponding performance parameter is proportional to a corresponding route point of the received location data depending on the value of the performance parameter.

Figure 4:
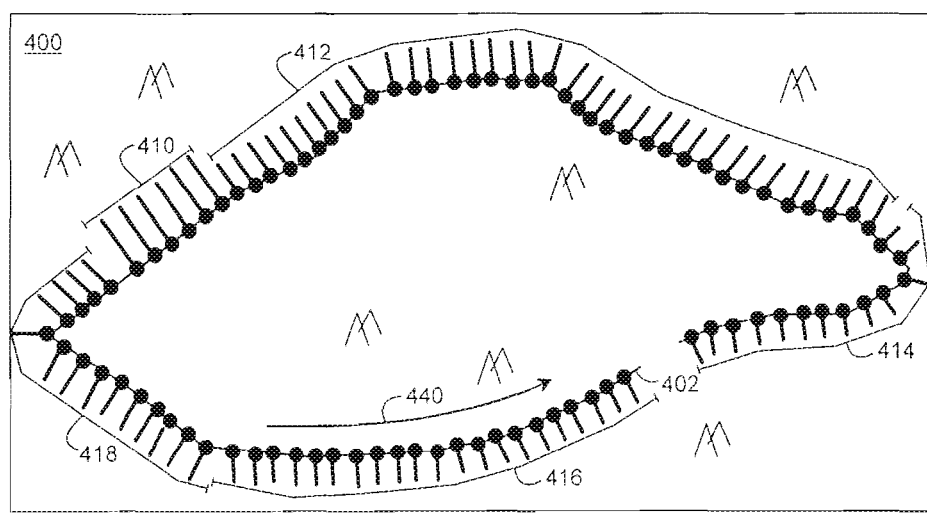
FIG. 4 shows an example of graphical data generation.

FIG. 4 shows an example of graphical data generation on a display window 400. The generated graphical data associated to the received location data is illustrated in FIG. 4 as route 402 that can be indicated on a map background. The rounded dots illustrate route points included in the route 402. The graphical data associated to the performance parameters are illustrated with graphical data items in groups 410, 412, 414, 416, 418, each group comprising graphical data items associated to corresponding route points. The graphical data items are illustrated in this example as thick lines having a certain spatial dimension, here in length that depends on the value of the performance parameter measured at that route point. For example, if the performance parameter measured is a heart rate, then the length of the graphical data item (thick line) may be adjusted on the basis of the heart rate value. In this example, the longer lines as illustrated by the graphical data items in group 410, may be indicative of a high heart rate and the shorter lines as illustrated by the graphical data items in group 416 may be indicative of a low heart rate. The arrow 440 illustrates the travelling direction in this example.

In addition, different colors can be used in the graphical data items for example to indicate having optimal vs. unoptimal heart rate value levels at certain parts of the route or to indicate being above or below certain predetermined threshold values. Also the color of the route line 402 and/or route points could be changed according to predetermined parameter values or thresholds. For example, a blue color may indicate the user of a slow speed, a green color may indicate that a normal speed is used, and a red color may indicate that a fast speed is used.

By having graphical data items with adjustable spatial dimensions to indicate certain performance parameter values, it is easy to monitor one's exercise performance that took place on a certain route. There is no need to memorize meanings of certain colors because, for example, the graphical data items of certain spatial dimensions indicative of corresponding values of performance parameters can easily be used to check heart rate levels.

The graphical data can be indicated in many different ways such as by using lines, columns, pillars, dots, figures or any combinations thereof. For example a single line travelling at a certain spatial distance from the corresponding route points can be used to illustrate the performance parameter values on the route travelled.

In an embodiment, the processing unit 110 is configured to adjust the size of each graphical data item associated to a performance parameter on the basis of the value of the performance parameter. Thus, in addition to the length, the width of a graphical data item may be adjusted according to the value of the corresponding performance parameter.

Figure 5:
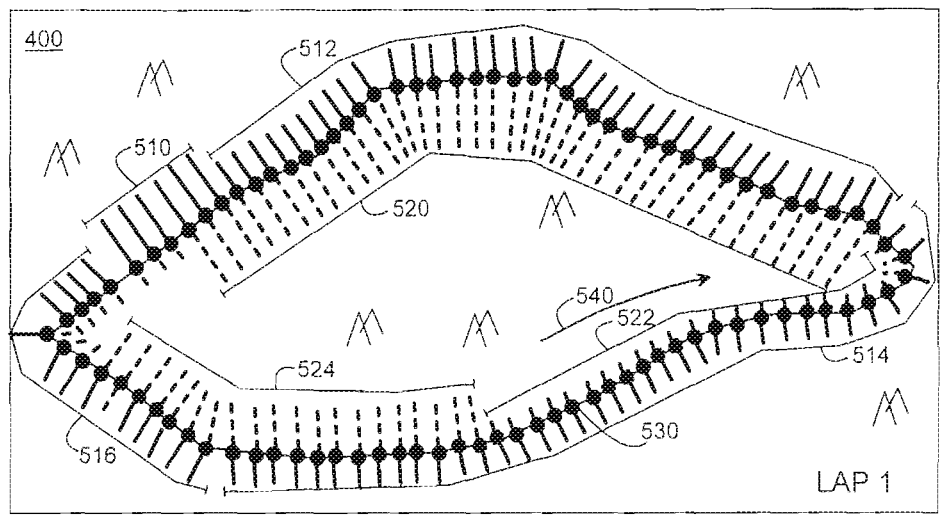
FIG. 5 shows another example of graphical data generation.

FIG. 5 shows another example of graphical data generation. The rounded dots illustrate route points included in the route travelled. The graphical data associated to the performance parameters are illustrated with graphical data items of graphical data item groups 510, 512, 514, 516. The arrow 540 illustrates the travelling direction in this example.

In an embodiment, two or more different performance parameters, e.g. heart rate and speed, may be indicated by using graphical data items extending on both sides of the indicated graphical data associated to the location data. In FIG. 5 the first performance parameters, e.g. heart rate, is illustrated by the graphical data items in groups 510, 512, 514, 516 (solid lines), and the second performance parameters, e.g. speed, is illustrated by the graphical data items in groups 520, 522, 524 (dashed lines). This way information on different performance parameters can be easily added to the generated graphical data in a user-friendly manner.

In an embodiment, the processing unit 110 is configured to generate two or more separate graphical data associated to the received location data and to the corresponding performance parameters for each determined recurring route, wherein each recurring route is formed by successive route points substantially overlapping with successive route points of other recurring routes of the received location data.

Figure 6:
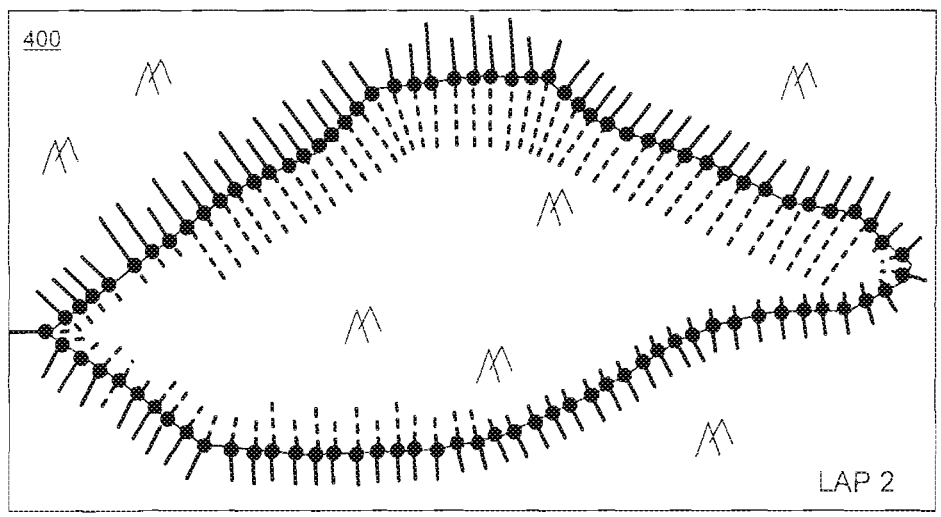
FIG. 6 shows another example of graphical data generation.

It is common that an exerciser follows the same overlapping route several times during the exercise. Thus, it is possible to generate separate graphical data for each of the recurring route, which makes it easy to monitor the performance data in each of the different routes. The examples of FIGS. 5 and 6 show two laps that have been travelled by the user. The processing unit 110 may be configured to detect a split point 530 that indicates the start of a recurring route for which the user wishes to have a separate graphical data generated. Determining the split point 530 can be an automatic function or it can be controlled by the user of the device.

The generated two or more separate graphical data for each determined recurring route may be indicated by using separate route graphs for each determined recurring route. The recurring route can also be a certain back and forth route between two points instead of laps that start and end at the same point.

Figure 7:
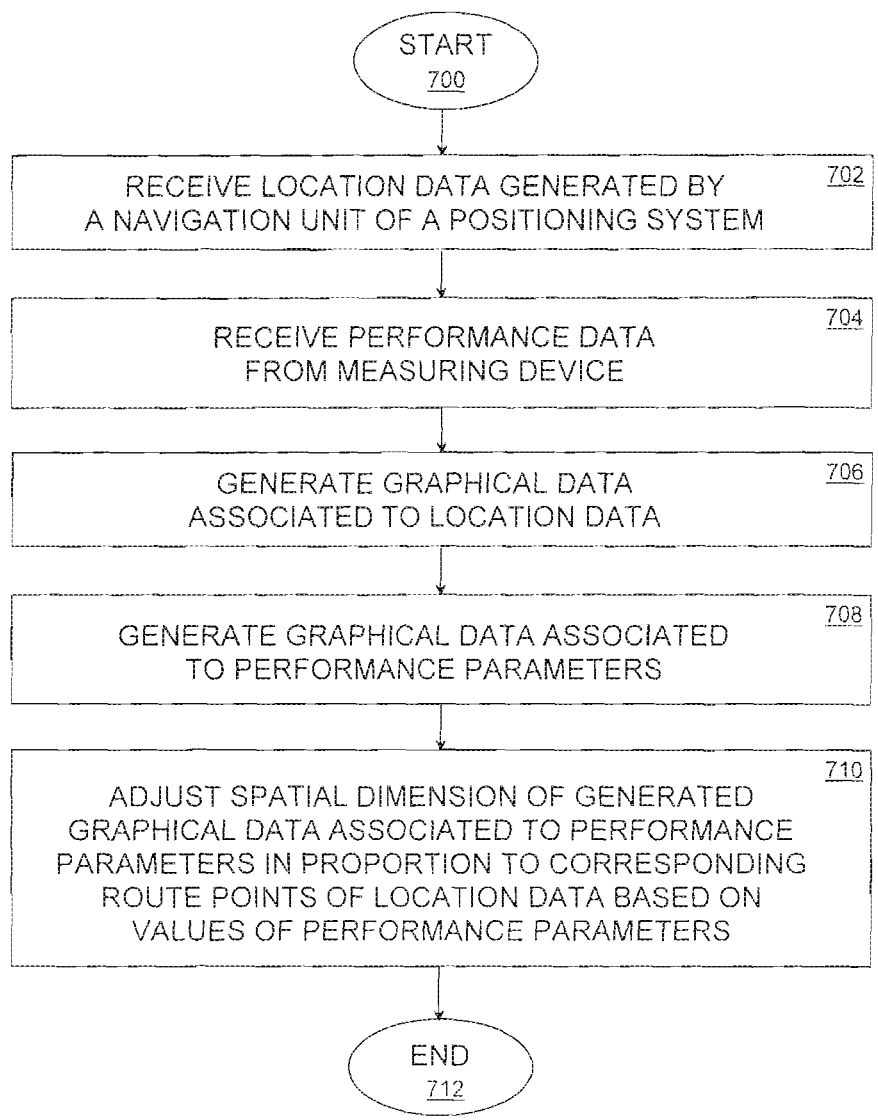
FIG. 7 shows an example of a method of generating graphical data.

FIG. 7 illustrates an example of a method of generating graphical data. The method starts in 700.

In 702, location data generated by a navigation unit of a positioning system (e.g. satellite positioning system, base station positioning system) is received.

In 704, performance data is received from a measuring unit. The performance parameters of the performance data are associated to corresponding route points included in the received location data.

In 706, graphical data associated to the received location data is generated.

In 708, graphical data associated to the performance parameters is generated.

In 710, the spatial dimension of the generated graphical data associated to the performance parameters is adjusted in proportion to the corresponding route points of the received location data on the basis of the values of the performance parameters.

The method ends in 712.

Figure 8:
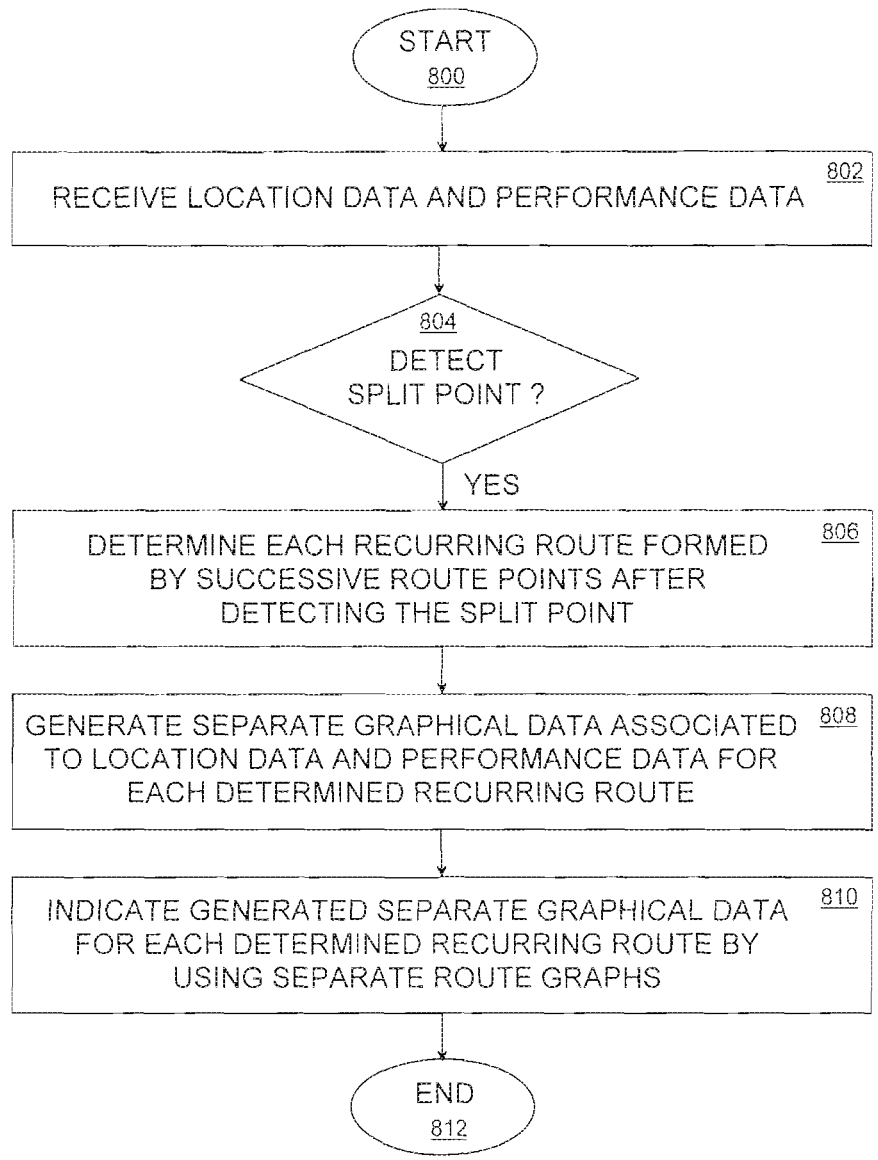
FIG. 8 shows another example of a method of generating graphical data.

FIG. 8 illustrates another example of a method of generating graphical data. The method starts in 800.

In 802, location data and performance data are received.

If a split point is detected in 804, then 806 is entered where each recurring route formed by successive route point is determined.

In 808, separate graphical data associated to the location data and to the performance data is generated for each determined recurring route.

In 810, the generated separate graphical data for each determined recurring route is indicated by using separate route graphs.

The method ends in 812.

The embodiments of the invention may be implemented in an electronic device comprising a processing unit including a graphic generator. The processing unit may be configured to perform at least some of the steps described in connection with the flowchart of FIGS. 7 and 8 and in connection with FIGS. 1 to 6. The embodiments may be implemented as a computer program comprising instructions for executing a computer process for generating graphical data. The computer process according to an embodiment comprises: receiving location data generated by a navigation unit of a positioning system, receiving performance data from a measuring unit, wherein performance parameters of the performance data are associated to corresponding route points included in the received location data, generating graphical data associated to the received location data, generating graphical data associated to the performance parameters, and adjusting the spatial dimension of the generated graphical data associated to the performance parameters in proportion to the corresponding route points of the received location data on the basis of the values of the performance parameters.

The computer program may be stored on a computer program distribution medium readable by a computer or a processor. The computer-readable program medium may be, for example but not limited to, an electric, magnetic, optical, infrared or semiconductor system, device or transmission medium. The computer program medium may include at least one of the following media: a computer readable medium, a program storage medium, a record medium, a computer readable memory, a random access memory, an erasable programmable read-only memory, a computer readable software distribution package, a computer readable signal, a computer readable telecommunications signal, computer readable printed matter, and a computer readable compressed software package.

It will be obvious to a person skilled in the art that, as the technology advances, the inventive concept can be implemented in various ways. The invention and its embodiments are not limited to the examples described above but may vary within the scope of the claims.

What is claimed is:

1. An electronic device, comprising:
  a receiving unit configured to receive location data generated by a navigation unit of a positioning system, and to receive performance data from a measuring unit, wherein performance parameters of the performance data are associated to corresponding route points included in the received location data and wherein the performance data is associated with one or more physiological levels and any ratio thereof, and a style of propagation;
  a graphic generator configured to generate graphical data associated to the received location data, wherein the graphic generator is further configured to generate graphical data associated to the performance parameters, and to adjust the spatial dimension of the generated graphical data associated to the performance parameters on the basis of the values of the performance parameters measured at the corresponding route points of the received location data;
  wherein the graphical data associated to the performance parameters indicates two or more different performance parameters by using graphical data items attached to and extending from both sides of an indicated graphical data item associated to the location data corresponding to the two or more different performance parameters; and
  a display unit that displays the received location data, wherein the graphical data items associated to corresponding route points are configured and displayed in accordance with an adjustable spatial dimension, wherein the spatial dimension varies based on the value of the performance data at a particular route point.

2. The electronic device of claim 1, wherein the graphic generator is further configured to generate graphical data including graphical data items associated to the performance parameters, wherein the spatial dimension of each graphical data item associated to the corresponding performance parameter is proportional to the value of the performance parameter measured at the corresponding route points of the received location data.

3. The electronic device of claim 2, wherein the graphic generator is further configured to adjust the size of each graphical data item associated to a performance parameter on the basis of the value of the performance parameter.

4. The electronic device of claim 1, wherein the graphic generator is further configured to include instructions on the details of the graphics in the generated graphical data associated to the received location data and the generated graphical data associated to the performance parameters.

5. The electronic device of claim 4, wherein the graphical data associated to the performance parameters includes instructions on indicating the graphical data associated to the performance parameters in the form of at least one of the following graphical data items: a column, a pillar, a line, a point, a pattern, or any combinations thereof.

6. The electronic device of claim 1, wherein the performance parameters comprise at least one of the following values: pedalling power, cadence, pace frequency, power level, step length, fitness value, body temperature, colliquation state, performance capacity index, lactic acid state, or any ratio thereof, or any combination thereof.

7. The electronic device of claim 1, wherein the graphic generator is further configured to generate two or more separate graphical data items associated to the received location data and to the corresponding performance parameters for each determined recurring route, wherein each recurring route is formed by successive route points substantially overlapping with successive route points of other recurring routes of the received location data.

8. The electronic device of claim 7, wherein the graphic generator is further configured to include instructions in the ingenerated graphical data on indicating the generated two or more separate graphical data items for each determined recurring route by using separate route graphs for each determined recurring route.

9. A method of generating graphical data, the method comprising:
receiving location data generated by a navigation unit of a positioning system;
receiving performance data from a measuring unit, wherein performance parameters of the performance data are associated to corresponding route points included in the received location data and wherein the performance data is associated with one or more physiological levels and any ratio thereof, and a style of propagation;
generating graphical data associated to the received location data;
generating graphical data associated to the performance parameters;
adjusting the spatial dimension of the generated graphical data associated to the performance parameters on the basis of the values of the performance parameters measured at the corresponding route points of the received location data;
indicating two or more different performance parameters in the graphical data associated to the performance parameters by using graphical data items attached to and extending from both sides of an indicated graphical data item associated to the location data corresponding to the two or more different performance parameters; and
displaying the received location data, wherein the graphical data items associated to corresponding route points are configured and displayed in accordance with an adjustable spatial dimension, wherein the spatial dimension varies based on the value of the performance data at a particular route point.

10. The method of claim 9, further comprising generating graphical data including graphical data items associated to the performance parameters, wherein the spatial dimension of each graphical data item associated to the corresponding performance parameter is proportional to the value of the performance parameter measured at the corresponding route points of the received location data.

11. The method of claim 10, further comprising adjusting the size of each graphical data item associated to a performance parameter on the basis of the value of the performance parameter.

12. The method of claim 9, further comprising including instructions on the details of the graphics in the generated graphical data associated to the received location data and the generated graphical data associated to the performance parameters.

13. The method of claim 12, further comprising including instructions in the graphical data associated to the performance parameters on indicating the graphical data associated to the performance parameters in the form of at least one of the following graphical data items: a column, a pillar, a line, a point, a pattern, or any combinations thereof.

14. The method of claim 9, wherein the performance parameters comprise at least one of the following values: pedalling power, cadence, pace frequency, power level, step length, fitness value, body temperature, colliquation state, performance capacity index, lactic acid state, or any ratio thereof, or any combination thereof.

15. The method of claim 9, further comprising generating two or more separate graphical data items associated to the received location data and to the corresponding performance parameters for each determined recurring route, wherein each recurring route is formed by successive route points substantially overlapping with successive route points of other recurring routes of the received location data.

16. The method of claim 15, further comprising including instructions in the graphical data on indicating the generated two or more separate graphical data items for each determined recurring route on a display by using separate route graphs for each determined recurring route.

17. A non-transitory computer-readable distribution medium to store instructions that, when executed by a processing device, performs a computer process, the process comprising:
receiving location data generated by a navigation unit of a positioning system;
receiving performance data from a measuring unit, wherein performance parameters of the performance data are associated to corresponding route points included in the received location data and wherein the performance data is associated with one or more physiological levels and any ratio thereof, and a style of propagation;
generating graphical data associated to the received location data, wherein the process further comprising:
generating graphical data associated to the performance parameters;
adjusting the spatial dimension of the generated graphical data associated to the performance parameters on the basis of the values of the performance parameters measured at the corresponding route points of the received location data;
indicating two or more different performance parameters in the graphical data associated to the performance parameters by using graphical data items attached to and extending from both sides of an indicated graphical data item associated to the location data corresponding to the two or more different performance parameters; and
displaying the received location data, wherein the graphical data items associated to corresponding route points are configured and displayed in accordance with an adjustable spatial dimension, wherein the spatial dimension varies based on the value of the performance data at a particular route point.

18. The non-transitory computer-readable distribution medium of claim 17, wherein the performance parameters comprise at least one of the following values: pedalling power, cadence, pace frequency, power level, step length, fitness value, body temperature, colliquation state, performance capacity index, lactic acid state, or any ratio thereof, or any combination thereof.

19. The non-transitory computer-readable distribution medium of claim 17, wherein the process further comprises generating two or more separate graphical data items associated to the received location data and to the corresponding performance parameters for each determined recurring route, wherein each recurring route is formed by successive route points substantially overlapping with successive route points of other recurring routes of the received location data.

20. The non-transitory computer-readable distribution medium of claim 19, wherein the process further comprises including instructions in the graphical data on indicating the generated two or more separate graphical data items for each determined recurring route on a display by using separate route graphs for each determined recurring route.

21. The non-transitory computer-readable distribution medium of claim 17, wherein the distribution medium comprises at least one of the following media: a computer readable medium, a program storage medium, a record medium, a computer readable memory, a computer readable software distribution package, a computer readable telecommunications signal, and a computer readable compressed software package.

* * * * *